United States Patent [19]

McRae

[11] 4,082,538
[45] Apr. 4, 1978

[54] SELECTIVE WEED CONTROL WITH M-DINITROBENZENE

[75] Inventor: Dougal Harold McRae, Hatboro, Pa.

[73] Assignee: Rohm and Haas Company, Philadelphia, Pa.

[21] Appl. No.: 368,374

[22] Filed: Jun. 8, 1973

Related U.S. Application Data

[63] Continuation-in-part of Ser. No. 67,199, Aug. 26, 1970, abandoned.

[51] Int. Cl.$^2$ .............................................. A01N 9/20
[52] U.S. Cl. ............................................. 71/125; 71/93; 71/100; 71/115; 71/117; 71/120; 71/121; 71/122; 71/124
[58] Field of Search ........................................ 71/125

[56] References Cited

U.S. PATENT DOCUMENTS 3,328,155  6/1967  Walworth .............................. 71/125

FOREIGN PATENT DOCUMENTS 1,481,868  2/1965  Japan ................................... 71/125

OTHER PUBLICATIONS

Jones, et al., J. Sci. Food Agric., 5, pp. 38–43, (1954).

*Primary Examiner*—Glennon H. Hollrah
*Attorney, Agent, or Firm*—Bernard J. Burns; George W. F. Simmons; William E. Lambert

[57] ABSTRACT

Weeds can be controlled by the application as a herbicide of m-dinitrobenzene. This compound is particularly effective for selectively controlling weeds in agronomic crops.

5 Claims, No Drawings

SELECTIVE WEED CONTROL WITH M-DINITROBENZENE

CROSS-REFERENCE TO RELATED APPLICATION

This application is a continuation-in-part of copending U.S. Pat. application Ser. No. 67,199, filed on Aug. 26, 1970 now abandoned.

This invention relates to novel methods for controlling the growth of weeds, such as in agronomic crops, and to novel herbicidal compositions.

Many compounds active as herbicides have been described in the prior art. However, the herbicidal effectiveness of a given compound cannot usually be predicted from an examination of the substituent groups of the compound and often quite closely related compounds will have quite different weed control abilities. Various herbicides may have overlapping or complementary areas of activity or selectivity, and can thus be useful in combination to control a variety of weeds upon application of a single composition. Furthermore, the various known herbicides are not completely effective. An ideal herbicide should give selective weed control, over the full growing season, with a single administration at low rates of application, and at as low a cost as possible. It should be able to control all common weeds by killing them as the seed, the germinating seed, the seedling, and the growing plant. At the same time, the herbicide should not be phytotoxic to the crops to which it is applied and should decompose or otherwise be dissipated so as not to contaminate the soil permanently. Known herbicides fall short of these ideals, and it would thus be desirable to have new herbicides which show even more selective control of undesirable plants among desirable crops, which complement known herbicides in activity, or which have other advantages such as reduced rate of application or reduced cost.

It has now been unexpectedly found that m-dinitrobenzene controls the growth of weeds. In one embodiment of the invention, m-dinitrobenzene has been found to be particularly effective for selectively controlling weeds in agronomic crops.

m-Dinitrobenzene is useful both as a preemergence and as a postemergence herbicide. Preemergence herbicides are ordinarily used to treat the soil in which the desired crop is to be planted by application either before seeding, during seeding, or, as in most applications, after seeding and before the crop emerges, so as to prevent the emergence of any weeds. Postemergence herbicides are those which are applied after the plants have emerged and during their growth period.

In crops which are commonly transplanted during their growth period and which are tolerant to m-dinitrobenzene when applied postemergence, the m-dinitrobenzene can conveniently be applied to the crop after transplantation, and prior to the emergence of weeds in the transplanted crop. Among the transplanted crops in which m-dinitrobenzene can be used is rice.

Among the crops which show either preemergence or postemergence tolerance to m-dinitrobenzene and in which this compound can be used as a herbicide are barley, corn, soybeans, wheat, peanuts, cotton, radishes, peas, alfalfa, cucumbers, rice, sorghum, sugarbeets, and rape. The m-dinitrobenzene is particularly useful in controlling the growth of monocotyledonous weeds in these crops.

The herbicide of the invention can be applied to the soil or to crops in any amount which will give the required control of weeds. A preferred rate of application is from about 0.5 to about 20 pounds of m-dinitrobenzene per acre, and most preferably from about 1 to about 8 pounds per acre.

The herbicide of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. The herbicidal compositions of the invention can be either solid or liquid formulations or solutions. For example, the m-dinitrobenzene can be formulated as a wettable powder, an emulsifiable concentrate, a dust, a granular formulation, an aerosol, or a flowable emulsion concentrate. In such formulations, the compound is extended with a liquid or solid carrier and, when desired, suitable surfactants are incorporated.

It may be desirable in some applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual".

The herbicide of the invention can be dissolved in any appropriate solvent. Examples of solvents which are useful in the practice of the invention include alcohols, ketones, aromatic hydrocarbons, dimethylformamide, dioxane, dimethyl sulfoxide, and the like. Mixtures of these solvents can also be used. The concentration of the solution can vary from about 2% to about 98% by weight of the active ingredient with a preferred range being about 25% to about 75%.

For the preparation of emulsifiable concentrates, the m-dinitrobenzene can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 25% by weight and in flowable emulsion concentrates, this can be as high as about 75%.

Wettable powders suitable for spraying, can be prepared by admixing the active compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, and preferably about 40% to 75%. A dispersing agent can constitute about 0.5% to about 3% by weight of the composition, and a wetting agent can constitute from about 0.1% to about 5% of the composition.

Dusts can be prepared by mixing the compound of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% by weight of the active ingredient are commonly made and are subsequently diluted to about 1% to 10% as a use concentration.

Granular formulations can be prepared by impregnating a solid such as granular fuller's earth, vermiculite, ground corn cobs, seed hulls, including bran or other grain hulls, or similar material. A solution of m-dinitrobenzene in a volatile organic solvent can be sprayed or mixed with the granular solid and the solvent then removed by evaporation. The granular material can have any suitable size, with a preferable size range of 16 to 60 mesh. The m-dinitrobenzene will usually comprise about 2 to 15% by weight of the granular formulation.

The herbicide of the invention can also be mixed with fertilizers or fertilizing materials before application. In one type of solid fertilizing composition in which the m-dinitrobenzene can be used, particles of a fertilizer or fertilizing ingredients, such as ammonium sulfate, ammonium nitrate, or ammonium phosphate, can be coated with the herbicide. The m-dinitrobenzene and solid fertilizing material can also be admixed in mixing or blending equipment, or can be incorporated with fertilizers in granular formulations. Any relative proportion of herbicide and fertilizer can be used which is suitable for the crops and weeds to be treated. The herbicide will commonly be from about 5% to about 25% by weight of the fertilizing composition. These compositions provide fertilizing materials which promote the rapid growth of desired plants, and at the same time control the growth of undesired plants.

When used as a preemergence herbicide, m-dinitrobenzene can be applied to the growth medium before the emergence of the weeds to be controlled by preplant soil incorporated application, by surface applications, or by any other convenient technique.

The m-dinitrobenzene can be applied as a preemergence or postemergence herbicidal spray by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated, and the weeds to be controlled, and the like.

For some applications, it may be desirable to add one or more other herbicides along with the m-dinitrobenzene. Examples of other herbicides which can be incorporated to provide additional advantages and improved effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-(4-chlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine 2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)2,6-dinitro-4-methylaniline
N,N-di(n-propyl)-2,6-dinitro-4-methylsulfonylaniline
O-(2,4-dichlorophenyl)-O-methyl-isopropylphosphoramidothioate
[4-amino-3,5,6-trichloropicolinic acid
2,3-dichloro-1,4-naphthoquinone
di(methoxythiocarbonyl)disulfide
6,7-dihydrodipyridol [1,2-a:2',1'-c]pyrazidinium salts
1,1'-dimethyl 4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired. Particularly useful combinations include m-dinitrobenzene with any of the following herbicides: dinitro-o-(sec-butyl)phenyl and its salts, 2,4-dichloro-4'nitrodiphenyl ether, triazines such as 2-chloro-4-ethylamino-6-isopropylamino-s-triazine, 3-amino-2,5-dichlorobenzoic acid, urea compounds such as 3-(3,4-dichlorophenyl)-1,1-dimethylurea and 3-(3,4-dichlorophenyl)-1-methoxy-1-methylurea, 2-chloro-2',6'-diethyl-N-(methoxymethyl)acetanilide, S-ethyl dipropyl-thiocarbamate, trifluoro-2,6-dinitro-N,N-dipropyl-p-toluidine, and 4-(methylsulfonyl)-2,6-dinitro-N,N-dipropylaniline.

The compound m-dinitrobenzene is known in the prior art and can be prepared by any of the known methods. One convenient preparative route is the direct nitration of benzene with concentrated nitric acid in the presence of concentrated sulfuric acid.

The following examples will further illustrate this invention but are not intended to limit it in any way.

EXAMPLE 1

This example shows the herbicidal activity of m-dinitrobenzene towards a number of common weeds. Using the procedure described below, m-dinitrobenzene was evaluated for control of the following plants:

smartweed (*Polygonum spp.*)
crabgrass (*Digitaria spp.*)
foxtail (*Setaria faberii*)
millet (*Setaria italica*)
ryegrass (*Lolium perenne*)
wild oat (*Avena fatua*)
mustard (*Brassica haber*)
wild carrot (*Daucus carota*)
lambsquarters (*Chenopodium album*)
curly dock (*Rumex crispus*)
velvetleaf (*Abutilon theophrasti*)
pigweed (*Amaranthus retroflexus*)
barnyardgrass (*Echinochloa crusgalli*)
downy brome (*Bromus tectorum*)
Johnsongrass (*Sorghum halepense*)
nutsedge (*Cyperus esculentus*)
quackgrass (*Agropyron repens*)
bindweed (*Convolvulus arvensis*)
cocklebur (*Xanthium pensylvanicum*)
morningglory (*Ipomoea purpurea*)
corn (*Zea mays*)
cotton (*Gossypium hirsutum*)
soybean (*Glycine max*)
rice (*Oryza sativa*)
tomato (*Lycopersicum esculentum*)
wheat (*Triticum vulgare*)
radish (*Raphanus sativus*)
sugarbeet (*Beta vulgaris*)
rape (*Brassica napus*)
Japanese millet (*Echinochloa frumentacea*)

The following test procedure is employed. Seeds of selected crops and weeds are planted in soil in flats. For preemergence tests, the flats are treated with the test compound immediately after the planting. For postemergence tests, two weeks after seeds are planted, the flats are treated with the test compound. The compound to be evaluated is sprayed over the flats using a carrier volume equivalent to 50 gallons per acre at the rate of application (pounds per are, lb/A.) specified in the tables. About two weeks after the application of the test compound, the state of growth of the plants is observed and the phytotoxic effect of the compound is evaluated. Tables I and II give the average percent control achieved by the m-dinitrobenzene in terms of the percent of the plants which are killed by the compounds.

TABLE I

| Preemergence Activity of m-Dinitrobenzene | | | | |
|---|---|---|---|---|
| | % Kill | | | |
| Plant | 2* | 4* | 8 | 16 |
| Barnyardgrass | 95 | 97 | 99 | 100 |
| Crabgrass | 100 | 100 | 100 | 100 |
| Downy Brome | 70 | 85 | 80 | 100 |

TABLE I-continued
Preemergence Activity of m-Dinitrobenzene

| | % Kill | | | |
|---|---|---|---|---|
| Plant | 2* | 4* | 8 | 16 |
| Foxtail | 99 | 100 | 100 | 100 |
| Johnsongrass | 55 | 50 | 30 | 80 |
| Nutsedge | 10 | 30 | 100 | 100 |
| Yellow Millet | 100 | 100 | 100 | 100 |
| Quackgrass | 40 | 85 | 80 | 90 |
| Ryegrass | 90 | 97 | 99 | 100 |
| Wild Oats | 15 | 20 | 30 | 50 |
| Bindweed | 30 | 45 | 70 | 80 |
| Cocklebur | 0 | 0 | — | — |
| Curly dock | 45 | 80 | 90 | 100 |
| Lambsquarters | 85 | 95 | 90 | 100 |
| Morningglory | 40 | 60 | 60 | 90 |
| Pigweed | 90 | 100 | 100 | 100 |
| Velvetleaf | 75 | 75 | 90 | 100 |
| Wild Carrot | 95 | 85 | 100 | 100 |
| Wild Mustard | 75 | 97 | 90 | 100 |
| Smartweed | 80 | 100 | — | — |
| Japanese Millet | 100 | 100 | 100 | — |
| Corn | 0 | 0 | 30 | 40 |
| Rice | 50 | 90 | 90 | 90 |
| Wheat | 0 | 10 | 0 | 20 |
| Cotton | 0 | 0 | 0 | 0 |
| Soybean | 0 | 10 | 60 | 80 |
| Tomato | 35 | 80 | 80 | 100 |
| Radish | 0 | 0 | 0 | — |
| Sugarbeet | 0 | — | — | — |
| Rape | 0 | 0 | — | — |

*Results of two tests

TABLE II
Postemergence Activity of m-Dinitrobenzene

| | % Kill | | | |
|---|---|---|---|---|
| Plant | 2* | 4* | 8 | 16 |
| Barnyardgrass | 50 | 45 | 60 | 90 |
| Crabgrass | 55 | 35 | 80 | 90 |
| Downy Brome | 20 | 10 | 70 | 100 |
| Foxtail | 65 | 75 | 70 | 90 |
| Johnsongrass | 25 | 40 | 40 | 90 |
| Nutsedge | 10 | 15 | 30 | 70 |
| Yellow Millet | 25 | 60 | 80 | 100 |
| Quackgrass | 10 | 10 | 20 | 90 |
| Ryegrass | 20 | 40 | 80 | 100 |
| Wild Oats | 10 | 35 | 40 | 80 |
| Bindweed | 40 | 50 | — | — |
| Cocklebur | 60 | 80 | 90 | 100 |
| Curly dock | 20 | 50 | 100 | 100 |
| Lambsquarters | 95 | 95 | 100 | 100 |
| Morningglory | 45 | 45 | 100 | 100 |
| Pigweed | 90 | 100 | 100 | 100 |
| Velvetleaf | 70 | 95 | 100 | 100 |
| Wild Carrot | 45 | 45 | 100 | 100 |
| Wild Mustard | 65 | 85 | 100 | 100 |
| Smartweed | 85 | 90 | 100 | 100 |
| Corn | 25 | 40 | 60 | 80 |
| Rice | 20 | 25 | 30 | 40 |
| Wheat | 15 | 35 | 30 | 40 |
| Cotton | 80 | 95 | 100 | 100 |
| Soybean | 30 | 40 | 50 | 50 |
| Tomato | 55 | 80 | 100 | 100 |

*Results of two tests

The above data demonstrates the effective herbicidal action of m-dinitrobenzene against a wide variety of monocotyledonous and dicotyledonous weeds, as well as the tolerance of crops such as corn, wheat, cotton, and soybeans to this herbicide.

EXAMPLE 2

This example shows the herbicidal activity of m-dinitrobenzene as compared to the activity of a number of closely related compounds. The following compounds were evaluated following the procedure of Example 1.

(I) m-dinitrobenzene
(II) p-dinitrobenzene
(III) o-dinitrobenzene
(IV) 1,2-dichloro-3,5-dinitrobenzene
(V) 2,4-dinitrochlorobenzene
(VI) 2,4-dinitrotoluene
(VII) 2,4-dinitrophenol
(VIII) 2,4-dinitroanisole
(IX) 1-nitro-3-nitrosobenzene Table III summarizes the comparative preemergence herbidical activity of the compounds tested, and Table IV summarizes their comparative postemergence activity.

TABLE III

Comparative Preemergence Activity

| Compound | lb/A | Barn-yard-grass | Crab-grass | Downy Brome | Fox-tail | John-son-grass | Nut-sedge | Quack-grass | Rye-grass | Wild Oat | Yellow Millet | Bind-weed | Cock-lebur | Curly dock | Lambs-quarters | Morning-glory | Pig-weed | Velvet-leaf | Wild carrot | Wild mustard | Smart-weed |
|---|---|---|---|---|---|---|---|---|---|---|---|---|---|---|---|---|---|---|---|---|---|
| (I) | 4 | 100 | 100 | 99 | 100 | 70 | 20 | 95 | 99 | 30 | 100 | 50 | 0 | 90 | 100 | 80 | 100 | 70 | 99 | 95 | 100 |
| (II) | 4 | 0 | 0 | 50 | 0 | 0 | 0 | 0 | 0 | 0 | 0 | 0 | 0 | 60 | 0 | 0 | 50 | 0 | 0 | 0 | 0 |
| (III) | 4 | 0 | 0 | 0 | 0 | 0 | 0 | 0 | 0 | 0 | 0 | 0 | 0 | 0 | 0 | 0 | 60 | 40 | 0 | 0 | 0 |
| (IV) | 4 | 0 | 0 | 0 | 0 | 0 | 0 | 0 | 0 | 0 | 0 | 0 | 0 | 0 | 0 | 0 | 70 | 0 | 0 | 0 | 0 |
| (V) | 4 | 0 | 80 | 50 | 99 | 40 | 0 | 20 | 0 | 0 | 100 | 0 | 0 | 40 | 0 | 0 | 40 | 0 | 0 | 0 | 0 |
| (VI) | 4 | 99 | 99 | 70 | 60 | 30 | 0 | 0 | 70 | 20 | 0 | 0 | 0 | 80 | 0 | 0 | 60 | 0 | 40 | 0 | 0 |
| (VII) | 4 | 60 | 0 | 0 | 90 | 40 | 0 | 0 | 0 | 0 | 100 | 0 | 0 | 0 | 70 | 0 | 100 | 0 | 70 | 70 | 0 |
| (VIII) | 4 | 0 | 100 | 20 | 0 | 0 | 0 | 0 | 0 | 0 | 0 | 0 | 0 | 0 | 0 | 0 | 90 | 0 | 0 | 0 | 0 |
| (IX) | 4 | 0 | 0 | 0 | 0 | 0 | 0 | 0 | 0 | 0 | — | 0 | 0 | 0 | 0 | 0 | 0 | 0 | 0 | 0 | 0 |

TABLE IV

Comparative Postemergence Activity

| Compound | lb/A | Barn-yard-grass | Crab-grass | Downy Brome | Fox-tail | John-son-grass | Nut-sedge | Quack-grass | Rye-grass | Wild Oat | Yellow Millet | Bind-weed | Cock-lebur | Curly dock | Lambs-quarters | Morning-glory | Pig-weed | Velvet-leaf | Wild carrot | Wild mustard | Smart-weed |
|---|---|---|---|---|---|---|---|---|---|---|---|---|---|---|---|---|---|---|---|---|---|
| (I) | 4 | 50 | 60 | 0 | 100 | 50 | 20 | 10 | 50 | 40 | 80 | 50 | — | 0 | 90 | 0 | 100 | 90 | 0 | 80 | 100 |
| (II) | 4 | 0 | 0 | 0 | 0 | 0 | 0 | 0 | 0 | 0 | 0 | 0 | 0 | 0 | 0 | 0 | 0 | 0 | 0 | 0 | 0 |
| (III) | 4 | 0 | 10 | 0 | 20 | 0 | 0 | 0 | 10 | 0 | 40 | 30 | 90 | 60 | 100 | 20 | 90 | 60 | 70 | 90 | 100 |
| (IV) | 4 | 0 | 40 | 0 | 100 | 20 | 0 | 0 | 10 | 10 | 20 | 50 | 30 | 0 | 100 | 0 | 100 | 80 | 80 | 100 | 100 |
| (V) | 4 | 0 | 40 | 0 | 100 | 10 | 10 | 0 | 0 | 0 | 30 | 50 | 100 | 100 | 30 | 60 | 100 | 99 | 50 | 80 | 100 |
| (VI) | 4 | 60 | 40 | 0 | 100 | 40 | 0 | 0 | 20 | 0 | 20 | 90 | — | 100 | 100 | 60 | 100 | 100 | 100 | 100 | 100 |
| (VII) | 4 | 30 | 30 | 0 | 90 | 20 | 0 | 0 | 0 | 0 | 20 | 0 | 10 | 0 | 0 | 0 | 20 | 20 | 20 | 20 | 0 |
| (VIII) | 4 | 0 | 0 | 0 | 0 | 0 | 0 | 0 | 0 | 0 | — | 0 | — | 0 | 0 | 0 | 0 | 0 | 0 | 0 | 0 |
| (IX) | 4 | 0 | 0 | 0 | 0 | 0 | 0 | 0 | 0 | 0 | — | 0 | 10 | 0 | 0 | 0 | 0 | 0 | 0 | 0 | 0 |

The above data demonstrates the unexpected selective preemergence activity against both monocots and dicots of m-dinitrobenzene when compared to its closely related isomers and analogues.

EXAMPLE 3

This example shows the herbicidal activity of combinations of m-dinitrobenzene with various known herbicidal compounds. Using the procedure described in Example 1, the following compounds were evaluated for preemergence activity in combination with m-dinitrobenzene.

(X) dinitro-o(sec-butyl)phenol
(XI) 2,4-dichloro-4'-nitrodiphenyl ether
(XII) 2-chloro-4-ethylamino-6-isopropylamino-s-triazine Tables V and VI summarize the preemergence herbicidal activity of these compounds alone and of combinations of these compounds with m-dinitrobenzene.

TABLE V

Preemergence Activity of Herbicidal Combinations Containing m-Dinitrobenzene

| Compound | lb/A | Barn-yard grass | Crab-grass | Downy Brome | Fox-tail | John-son grass | Nut-sedge | Quack-grass | Rye-grass | Wild Oat | Yellow Millet | Bind-weed | Cock-lebur | Curly dock | Lambs-quarters | Morning-glory | Pig-weed | Velvet-leaf | Wild carrot | Wild mustard | Smart-weed |
|---|---|---|---|---|---|---|---|---|---|---|---|---|---|---|---|---|---|---|---|---|---|
| (I) | 1 | 0 | 90 | 30 | 40 | 20 | 20 | 0 | 40 | 0 | 80 | 0 | 0 | 0 | 0 | 0 | 0 | 0 | 0 | 0 | 0 |
| (I) | 2 | 80 | 100 | 90 | 70 | 50 | 40 | 60 | 90 | 0 | 100 | 30 | 0 | 40 | 0 | 0 | 50 | 40 | 90 | 0 | 100 |
| (X) | 1 | 0 | 0 | 0 | 0 | 0 | 0 | 0 | 0 | 0 | 0 | 0 | 0 | 0 | 0 | 30 | 0 | 0 | 30 | 0 | 100 |
| (X) | 2 | 30 | 95 | 80 | 50 | 30 | 80 | 40 | 90 | 0 | 90 | 0 | 0 | 100 | 100 | 0 | 90 | 20 | 100 | 90 | 100 |
| (I+X) | 2+1 | 0 | 80 | 60 | 20 | 0 | 20 | 20 | 40 | 0 | 90 | 40 | 0 | 70 | 100 | 0 | 90 | 40 | 50 | 80 | 90 |
| (I+++X) | 1+++2 | 20 | 70 | 40 | 80 | 0 | 0 | 80 | 90 | 0 | 90 | 0 | 0 | 90 | 100 | 0 | 90 | 20 | 50 | 90 | 100 |
| (I++X) | 1++2 | 40 | 99 | 100 | 80 | 40 | 80 | 40 | 70 | 20 | 90 | 0 | 0 | 90 | 90 | 0 | 100 | 20 | 50 | 100 | 100 |
| (XI) | 2+2 | 60 | 95 | 40 | 100 | 90 | 40 | 80 | 90 | 30 | 100 | 0 | 0 | 100 | 100 | 0 | 0 | 20 | 0 | 0 | 100 |
| (I+X) | 1+1 | 90 | 100 | 80 | 90 | 100 | 0 | 60 | 90 | 30 | 100 | 0 | 0 | 100 | 100 | 0 | 100 | 20 | 40 | 0 | 100 |

TABLE VI

Preemergence Activity of Herbicidal Combinations Containing m-Dinitrobenzene

| Compound | lb/A | Barn-yard grass | Crab-grass | Downy Brome | Fox-tail | John-son grass | Nut-sedge | Quack-grass | Rye-grass | Wild Oat | Yellow Millet | Bind-weed | Cock-lebur | Curly dock | Lambs-quarters | Morning-glory | Pig-weed | Velvet-leaf | Wild carrot | Wild mustard | Smart-weed |
|---|---|---|---|---|---|---|---|---|---|---|---|---|---|---|---|---|---|---|---|---|---|
| (I) | 2 | 90 | 90 | 100 | 0 | 40 | 40 | 80 | 90 | 0 | 100 | 0 | 0 | 0 | 0 | 0 | 40 | 0 | 100 | 0 | 60 |
| (XII) | 1 | 30 | 30 | 80 | 100 | 30 | 0 | 0 | 30 | 40 | 0 | 0 | 0 | 0 | 0 | 0 | 100 | 30 | 90 | 50 | 100 |
| (I+XII) | 2+1 | 100 | 100 | 100 | 100 | 70 | 0 | 100 | 100 | 50 | 100 | 0 | 0 | 100 | 100 | 0 | 100 | 50 | 100 | 50 | 100 |

Corn, wheat, peanuts, peas, cotton, alfalfa, and cucumbers showed complete or nearly complete tolerance to the above-tested combinations of compound I with compound X. Corn, rice, wheat, peanuts, peas, cotton, sugarbeets, tomatoes, alfalfa, and cucumbers showed complete or nearly complete tolerance to the above-tested combinations of compound I with compound XI. Corn, wheat, peanuts, snap beans, cotton, and soybeans showed complete tolerance to the above-tested combination of compound I with compound XII.

Following the procedure of Example 1, m-dinitrobenzene was also found to display advantageous complementary herbicidal activity when used in combination with 3-amino-2,5-dichlorobenzoic acid, N-(1,1-dimethyl-2-propynyl)-3,5-dichlorobenzamide, N,N-di(n-propyl)-2,6-dinitro-4-trifluoromethylaniline, ethyl N,N-di(n-propyl)thiolcarbamate, 3-(3,4-dichlorophenyl)-1,1-dimethylurea, 3-(3,4-dichlorophenyl)-1-methoxy-1-methylurea, and N-(2,6-diethylphenyl)-N-methoxymethyl-2-chloroacetamide.

The above data demonstrates that m-dinitrobenzene can be advantageously combined with other herbicides to give particularly useful selective weed control.

It is to be understood that changes and variations may be made without departing from the spirit and scope of the invention as defined by the appended claims.

I claim:

1. A method of selectively controlling monocotyledonous weeds in corn or wheat which comprises applying to the surface of the growth medium, prior to the emergence of the weeds from the growth medium, m-dinitrobenzene at a rate of 0.5 to 20 lbs. per acre.

2. A method of selectively controlling dicotyledonous weeds in soybeans, cotton or rape which comprises applying to the surface of the growth medium, prior to the emergence of the weeds from the growth medium, m-dinitrobenzene at a rate of 0.5 to 20 lbs. per acre.

3. A method of controlling barnyardgrass in transplanted rice which comprises applying to the area to be treated m-dinitrobenzene at a rate of about 0.5 to about 20 pounds per acre.

4. A method of selectively controlling barnyardgrass, crabgrass, downy brome, foxtail, Japanese millet, yellow millet, quackgrass, or ryegrass in corn or wheat which comprises applying to the area to be treated m-dinitrobenzene at a rate of about 0.5 to about 20 pounds per acre.

5. A method of selectively controlling curly dock, lambsquarters, morningglory, pigweed, smartweed, velvetleaf, wild carrot, or wild mustard in soybeans, cotton, or rape which comprises applying to the area to be treated m-dinitrobenzene at a rate of about 0.5 to about 20 pounds per acre.

* * * * *